(12) United States Patent
Smith et al.

(10) Patent No.: US 8,955,387 B2
(45) Date of Patent: Feb. 17, 2015

(54) FATIGUE TEST ARRANGEMENT

(75) Inventors: Stephen J Smith, Derby (GB); Philip D Blavins, Derby (GB); Andrew T Backler, Derby (GB)

(73) Assignee: Rolls-Royce PLC, London (GB)

( * ) Notice: Subject to any disclaimer, the term of this patent is extended or adjusted under 35 U.S.C. 154(b) by 1042 days.

(21) Appl. No.: 12/919,811

(22) PCT Filed: Feb. 18, 2009
(Under 37 CFR 1.47)

(86) PCT No.: PCT/GB2009/000424
§ 371 (c)(1),
(2), (4) Date: Apr. 27, 2011

(87) PCT Pub. No.: WO2009/112797
PCT Pub. Date: Sep. 17, 2009

(65) Prior Publication Data
US 2013/0081476 A1    Apr. 4, 2013

(30) Foreign Application Priority Data
Mar. 12, 2008 (GB) .................................. 0804481.0

(51) Int. Cl.
  *G01N 3/32* (2006.01)
  *G01M 7/02* (2006.01)
  *G01N 3/36* (2006.01)
  *G01N 33/00* (2006.01)

(52) U.S. Cl.
  CPC .................. *G01N 3/32* (2013.01); *G01M 7/025* (2013.01); *G01M 7/027* (2013.01); *G01N 3/36* (2013.01);
(Continued)

(58) Field of Classification Search
  CPC ............... G01N 2203/0073; G01N 2203/0246

USPC .............. 73/577, 579, 583, 808, 570.5, 774, 73/1.79; 244/99.13, 99.14; 84/234; 33/344, 350, 448, 450; 29/896.93; 267/140, 140.2
See application file for complete search history.

(56) References Cited

U.S. PATENT DOCUMENTS 2,356,894 A    8/1944 Sims
2,500,764 A    3/1950 MacGeorge
(Continued)

FOREIGN PATENT DOCUMENTS

EP    1 895 288 A2    3/2008

OTHER PUBLICATIONS

British Search Report issued in British Application No. 0804481.0 dated Jul. 2, 2008.
(Continued)

*Primary Examiner* — Lisa Caputo
*Assistant Examiner* — Roger Hernandez-Prewit
(74) *Attorney, Agent, or Firm* — Oliff PLC

(57) ABSTRACT

High cycle fatigue testing is required with regard to a large number of components in order to evaluate their performance and capabilities. Typically such components are mounted such that an excitation mechanism such as through use of air jets can be utilized in order to stimulate vibration. In order to isolate a desired vibration mode generally, an isolation device is utilized. The isolation device presents an edge to a node within the component in order to inhibit vibration modes other than that of interest. Unfortunately, prior isolation elements tend to wear resulting in spurious results. By providing an isolation element within an isolation device, a fatigue test arrangement can be achieved in which both axial movement in the direction of a spring upon which the element is presented as well as lateral movement can be achieved.

14 Claims, 2 Drawing Sheets

(52) U.S. Cl.
CPC  *G01N 2033/0083* (2013.01); *G01N 2203/0042* (2013.01); *G01N 2203/0044* (2013.01); *G01N 2203/0048* (2013.01); *G01N 2203/0073* (2013.01); *G01N 2203/0246* (2013.01)
USPC .......................................................... 73/808

(56) References Cited

U.S. PATENT DOCUMENTS

| | | | |
|---|---|---|---|
| 2,644,331 A | * | 7/1953 | Loring ............................ 73/579 |
| 2,782,633 A | | 2/1957 | Stauss et al. |
| 2,917,265 A | * | 12/1959 | Markowski .............. 267/140.11 |
| 3,023,610 A | | 3/1962 | Prochazka |
| 3,421,369 A | * | 1/1969 | Freehauf .................... 73/862.53 |
| 3,550,434 A | * | 12/1970 | Garmhausen et al. .......... 73/579 |

OTHER PUBLICATIONS

International Search Report issued in International Application No. PCT/GB2009/000424 on Sep. 6, 2010.

Written Opinion of the International Searching Authority issued in International Application No. PCT/GB2009/000424 on Sep. 6, 2010.

\* cited by examiner

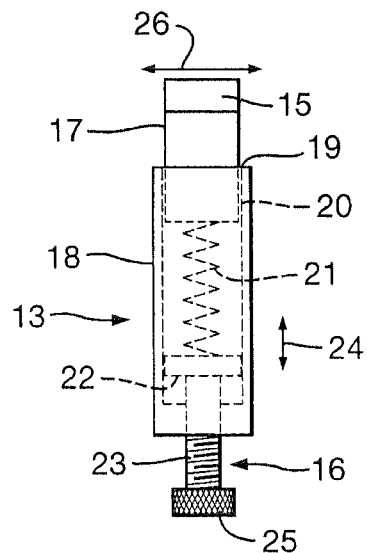
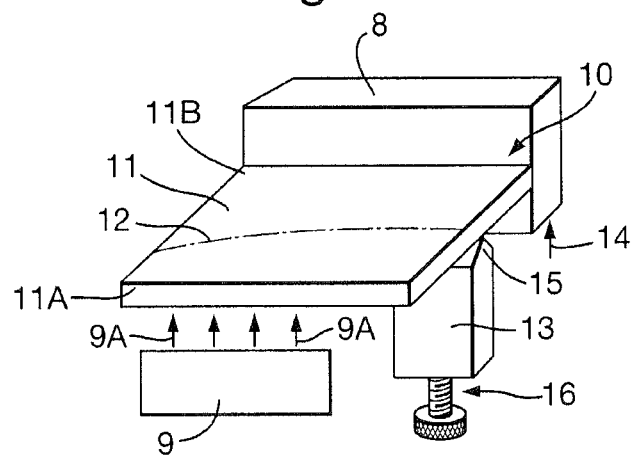

FATIGUE TEST ARRANGEMENT

The present invention relates to fatigue test arrangements and more particularly to fatigue test arrangements utilising vibration in order to test components such as aerofoils utilised in rotors of a gas turbine engine.

In a wide number of situations it is necessary to test and fully evaluate components in order to determine and predict life expectancy as well as capabilities of that component. There is particular concern in relation to fatigue testing. Fatigue test arrangements are provided which, for example, can comprise air excitation of a test component utilising high velocity air jets directed from nozzles towards the component, such as an aerofoil, to produce flutter in that component. Flutter in the component is controlled within a target mode of vibration via displacement and frequency measurement using a feedback control to an air valve regulating flutter inducing air jet incidence upon the test component. Such testing as indicated is utilised in order to evaluate components for machinery development, failure investigations, changes in processes, changes of manufacture and changes of material from which a component is made.

Within fatigue test arrangements it is known to provide an isolator or isolation devices to assist with regard to analysis of high cycle fatigue testing of components. The isolator is particularly associated with situations such as those with an aerofoil which have a peculiar shape and so may produce spurious results. Typically, the component such as an aerofoil is held in a mounting fixture and can be excited in a number of ways to produce a particular mode of vibration. Any mode of vibration higher than the first fundamental mode will have node lines which are stationary when the vibration mode is excited. An isolator is used to inhibit other modes of vibration and isolate the mode of interest by resting against a node line on the component such as an aerofoil causing that part of the aerofoil to be stationary and so encouraging the mode of vibration of interest to be excited when the method of excitation is switched on.

Current isolator devices generally comprise a cut rubber element held, rigidly in a clamp. The rubber element is cut to a point to engage the desired node line on the component. The isolation device in the form of the rubber element is rigidly located within the clamp and is pushed against the vibration node line of the component to, as indicated, isolate that mode of vibration requiring investigation.

The attached FIG. 4, marked 'Prior Art' illustrates a typical prior fatigue test arrangement. In such circumstances a component 1 typically in the form of an aerofoil is robustly presented and held in a presentation fixture 2. A vibration flutter inducing mechanism such as high velocity air jets 3, is presented to the component 1. In such circumstances as indicated above vibration node lines 4 are created within the component 1. In order to encourage particular excitation of the vibration mode of interest, an isolator device 5 in the form of an isolator 6 secured rigidly in a clamp 7 is provided. The isolator 6 as indicated, is formed from a cut pointed rubber element, rigidly held against the node line 4 such that that portion of the component is stationary.

The disadvantage with the prior fatigue test arrangement depicted in FIG. 4 is that as the isolator 6 is a substantially rigidly presented fixed rubber element, it increases the damping on the mode of vibration and is therefore prone to premature wearing. Furthermore, over time testing of a component may become unstable and may result in a loss of automatic control and accuracy as indicated above through the regulating air valve to the air jets causing flutter vibration in the component.

In accordance with aspects of the present invention there is provided a fatigue test arrangement comprising a vibration isolation device arranged in use relative to a component to be tested, the isolation device comprising a housing to provide an isolation element, the isolation element being suspended upon a spring element to allow axial displacement and the housing about the isolation element being arranged to allow lateral movement of the isolation element relative to the direction of axial displacement.

Further in accordance with aspects of the present invention there is provided an isolation device arrangement for a fatigue test arrangement, the isolation device arrangement comprising a housing to provide an isolation element, the isolation element being suspended upon a spring element to allow axial displacement and the housing about the isolation element being formed to allow lateral movement relative to the direction of axial displacement.

Typically, the spring is a mechanical coil spring, a hydraulic spring, a pneumatic spring or a foam element.

Generally, the isolation element is made from rubber. Typically, the isolation element has an edge or has a pointed end. Normally, the isolation element is captured within the housing. Generally, the isolation element projects from an isolation element end of the housing. Possibly, the isolation element end has a gap between the isolation element and an aperture in the isolation element end to allow the lateral movement. Additionally or alternatively the isolation element end is flexible to allow the lateral movement.

Generally the spring is arranged within the housing.

Generally, the arrangement includes a tensioner mechanism. Typically, the tensioner mechanism comprises a loading plate associated with the spring element and a displacement element to vary the load applied to the spring. The displacement element is a screw thread member.

Alternatively the spring is arranged outside the housing and the housing and the isolation element are suspended on the spring.

Generally, the arrangement incorporates a vibration excitation mechanism. Typically, the vibration excitation mechanism comprises at least one high velocity jet directed towards the component in use. Generally, the arrangement incorporates a plurality of high velocity jets directed towards a component. Typically, each jet is presented through a nozzle controlled by a respective valve. Possibly, each valve is associated with a control device and a sensor to determine vibration of the component and to vary the flow rate of the jet through the nozzle as required by adjusting the control valve.

Generally there are means to vibrate the component and means to hold an end of the component.

Aspects of the present invention will now be described by way of example and reference to the accompanying drawings in which:

FIG. 1 is a schematic illustration of an isolation device in accordance with aspects of the present invention; and, FIG. 2 is a schematic illustration of a fatigue test arrangement in accordance with aspects of the present invention.

Figure 3:
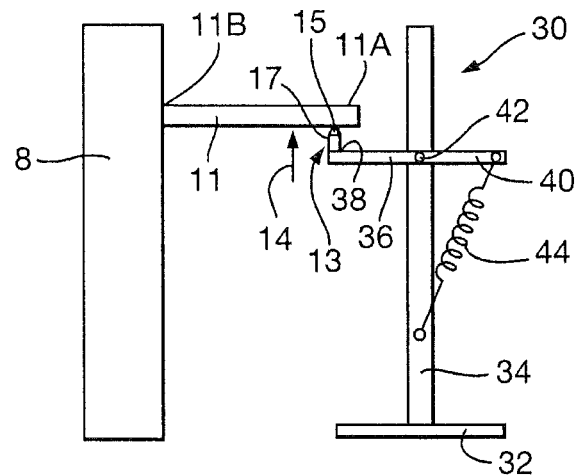
FIG. 3 is a schematic illustration of a further isolation device in accordance with aspects of the present invention.
Figure 4:
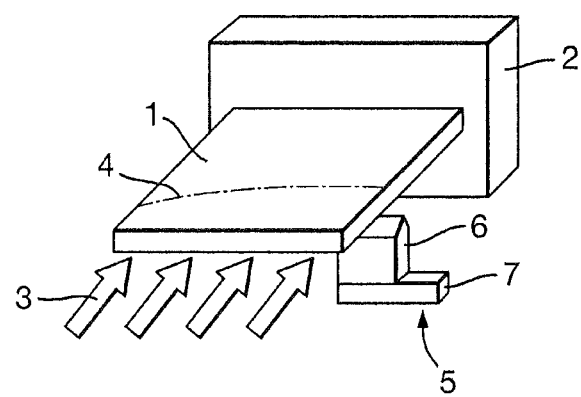
FIG. 4 is a schematic illustration of a prior fatigue test arrangement.

As indicated above, fatigue arrangements and in particular isolation devices utilised in accordance with aspects of the present invention are arranged to inhibit modes of vibration other than the mode of vibration of interest. However, inherently fatigue test arrangements are not perfect or ideal and, therefore, over time an isolation element within the test arrangement and isolation device will wear to allow other modes of vibration to be at least partially excited. It will be understood that it is very difficult to perfectly present the isolation element through its cut pointed edge upon the node line of the component and, therefore, some vibration will occur despite an abutment pressure presented to the component.

FIG. 2 provides a schematic illustration of a fatigue test arrangement 10 in accordance with aspects of the present invention. The arrangement 10 presents a component 11 which is vibrated into flutter, such that there is a node line 12 within the component 11. Typically, the component 11 is an aerofoil and as indicated above vibration and flutter is induced through high pressure air jets 9A presented to the aerofoil by an appropriate mechanism 9. The air jets are presented through nozzles with the rate of air flow regulated by a control valve. Thus, if a sensor is provided to determine levels of vibration and provide a signal to a controller dependent upon the level of vibration determined, it will be understood that the controller can adjust the control valves to present and regulate necessary air jet flow for the desired level of vibration in the component. It is to be noted that a first end 118 of the component 11 is held rigidly in a fixture 8, in the case of an aerofoil of a blade, this is the root of the blade. A second end 11A is unrestrained and free to vibrate.

In accordance with aspects of the present invention, an isolation device 13 is presented to the component 11 with an abutment pressure in the direction of arrowheads 14. To accurately apply the device 13 to achieve the desired isolation of vibration modes other than that of interest, the isolation device 13, as described above, generally comprises a rectangular block of rubber material cut and shaped to present an edge or a point 15 to the component 11 at a node line 12. Abutment pressure can be generated through tensioner arrangement or adjuster 16 as will be described later to achieve the correct degree of isolation of the vibration mode as required in accordance with aspects of the present invention.

In accordance with aspects of the present invention generally, a single spring loaded isolation element 17 as depicted in FIG. 1 is present upon a spring 21. Other than as required, the same reference numerals have been used in FIG. 1 as those used in FIG. 2 for comparison. The isolation element 17 as indicated above, is a rubber section member and presented within a body or housing 18, such that the isolation element 17 projects from an isolation element end 19 of the body 18. The isolation element 17 is generally captured within the isolation device 13 by an appropriate retention mechanism (not shown) or simply by position between a mounting for the isolation device 13 and the component 11 not shown in FIG. 1. It will be understood that if the isolation element 17 simply sits in an aperture 20 at the isolation element end 19 then the isolation element 17 can be simply removed and a new isolation element 17 inserted as required for each test episode or cycle period.

As indicated above, the housing 18 at least at the isolation element end 19 incorporates an aperture 20 to accommodate the isolation element 17. The isolation element 17 is suspended upon a spring 21. Thus the isolation element 17 inserted into the housing 18 upon the spring 21 can exert an abutment pressure through the edge 15 upon a component 11.

In order to develop and regulate, as well as adjust, the abutment pressure, the spring 21 generally itself, is presented upon a loading plate 22. The loading plate 22 is associated with a displacement mechanism 23 such that the loading plate 22 can be moved in the direction of arrowheads 24 to vary the load on the spring 21 and therefore, the responsiveness and pressure of the spring 21 and the abutment pressure applied by the isolation element 17 at the edge 15. The displacement mechanism 23 typically comprises a screw thread element with a knurled adjustment wheel 25. Generally the displacement mechanism 23 as part of a tensioner arrangement 16 is screwed or otherwise adjusted to displace the loading plate 22 until there is sufficient abutment force supplied through the edge 15. Once such abutment pressure is achieved the displacement mechanism 23 will be locked in position.

A particular advantage with regard to aspects of the present invention is that the isolation element 17 is allowed to move both axially, that is to say in the direction of the spring 21 or the housing 18 as well as laterally as shown by arrowheads 26. Such axial movement is achieved by allowing the isolation element 17 to move within the aperture 20 of the housing 18. Lateral movement or motion 26 is achieved by arranging that the isolation element 17 is a loose fit within the aperture 20 at least towards the isolation element end 19. An alternative might be to arrange for part of the housing 18 towards isolation element end 19 to be flexible to allow lateral motion but such configuration may add significantly to material and design requirements for the housing 18.

By allowing both axial movement and lateral movement 26, it will be understood that set up times with regard to fatigue test arrangements in accordance with aspects of the present invention will be significantly reduced as well as wear rates of the isolation element 17 and in particular the edge 15. It will be understood with prior arrangements where the isolation element essentially was clamped rigidly, such lateral motion was not possible and therefore the edge at the sharp contact point tended to slip and wear against the component surface as a result of other modes of vibration and flutter. By allowing a degree of lateral motion, early degradation of the isolation element 17 is reduced such that the isolation device in accordance with aspects of the present invention will avoid excitation of modes of vibration other than that desired for longer periods. In such circumstances, the fatigue test arrangement may operate for longer periods and avoid premature shut down when such other modes of vibration are detected.

Typically, a mechanical coil spring as depicted in FIG. 1 will be utilised in accordance with aspects of the present invention. However, other springs, such as hydraulic springs or pneumatic springs or foam elements may also be used.

By aspects of the present invention, a spring loaded isolation element 17 with a point or an edge 15 is utilised in engagement with a component 11 to isolate a particular mode of vibration. The isolation device presents generally a rectangular cut rubber section as an isolation element. Whilst providing an edge to the isolation element and an abutment pressure, the isolation element is suspended upon the spring to inhibit movement at any required point on the component such as a rotor blade aerofoil, to allow better excitation of the component in the desired vibration mode. The arrangement and isolation device in accordance with aspects of the present invention allows axial movement as well as lateral motion of the isolation element 17 for better responsiveness to fatigue testing conditions. Furthermore, by provision of a tensioner arrangement 16 it will be understand that the load applied through the rubber isolation element at an abutment pressure can be adjusted to a desired value dependent upon the severity of excitation vibration used whilst provision of the spring 21 will ensure that contact between the isolation element 17 and the aerofoil 11 is maintained.

By aspects of the present invention, particular advantages are achieved with respect to increasing isolation element life as well as the stability of fatigue testing for longer periods of time without detrimental degradation in the isolation element.

Furthermore, through use of robust abutment force whilst allowing for lateral motion and axial movement, better vibration mode isolation is achieved, whilst reducing fatigue test set up times. It will be understood that high cycle fatigue testing techniques require relatively long term presentation of excitation through air jets or otherwise, to a component. In such circumstances, confidence with regard to isolation elements and in particular consistent presentation of engagement edges of the isolation elements is important for consistent fatigue testing over that high cycle fatigue testing regime time period.

It will be understood the grade of rubber utilised with regard to the isolation element as well as its particular edge or point configuration, will be chosen dependent upon operational requirements. Furthermore, the extent by which the isolation element 17 extends beyond the housing 13 will also be chosen in order to achieve the desired lateral motion range, as well as presentation of an abutment force by the edge 15 to the component 11. It is also understood for capture and anchoring purposes, an adequate depth of the isolation element 17 into the aperture 20 of the housing 13 will also generally be required. Typically, as indicated, the element 17 will be readily interchangeable and comprise a rectangular cross section piece of rubber cut and shaped to provide the edge 15. However, if required different cross sections of rubber or elastomeric material may be utilised to form the isolation element and to achieve the desired lateral motion and/or anchoring to the housing 13 in accordance with aspects of the present invention.

As illustrated in FIG. 1 a single spring 21 will normally be utilised within the housing 13. However, where possible, more than one spring may be utilised to support a greater width or breadth of isolation element and so presented edge 15.

Modifications and alterations to aspects of the present invention will be appreciated by those skilled in the technology. Thus, as indicated above, generally a gap will be provided between the aperture 20 and the isolation element 17 towards the isolation element end 19 of the isolation device 13. This gap may be consistent at least in a relaxed state along the range of overlap between the element 17 and the aperture 20. Alternatively, the gap may be arranged to widen or narrow towards or away from the isolation element end 19 to facilitate lateral motion. It will also be understood that to allow a universal housing 18 to be used with different isolation element sizes or types or for different lateral motion ranges, the isolation element end may be constituted by a ferrule collar located within the housing 18 in order to vary the size of the aperture 20 and therefore the gap between the element 17 and the then formed aperture. It will also be understood that such ferrules may be formed from a material of desired flexibility to again define a range of lateral motion 26 by deformation of the ferrule.

FIG. 3 provides a schematic illustration of a further fatigue test arrangement 30 in accordance with aspects of the present invention. The arrangement 30 provides a component 11 which is vibrated into flutter, such that there is a node line within the component 11. Typically the component 11 is an aerofoil and as indicated above vibration and flutter is induced through high pressure air jets (not shown) directed onto the aerofoil. An isolation device 13 is arranged to abut the component 11 with an abutment pressure in the direction of arrowhead A. To achieve isolation of vibration modes other than that of interest the isolation device 13 comprises an isolation element 17, a rectangular block of rubber material, cut and shaped to present an edge or a point 15 to the component 11 at a node line.

The isolation device 13 is mounted upon a framework comprising a base member 32 and a depending member 34. Generally the base member 32 is arranged horizontally and the depending member 34 extends vertically from the base member 32. A beam 36 is pivotally mounted on the depending member 34 by a pivot 42 and the beam 36 has a first end 38 and a second end 40. The isolation device 13 is mounted within an aperture or a recess, in the first end 38 of the beam 36 and the isolation element 17 projects from the recess in the first end 38 of the beam 36. The isolation element 17 may simply sit in the recess in the first end 38 of the beam 36 so the isolation element 17 may be simply removed and a new isolation element 17 inserted as required for each test episode or cycle period. The isolation element 17 is allowed to move longitudinally relative to the beam 36, that is by allowing the isolation element 17 to move within the recess in the first end 38 of the beam 36 i.e. by providing a loose fit. Thus the isolation element 17 is allowed to move in a direction towards or away from the second end 40 of the beam 36.

A tension spring 44 is secured at a first end to the second end 40 of the beam 36 and a second end of the tension spring 44 is secured to the depending member 34 at a suitable point between the base member 32 and the pivot 42. The test arrangement 30 is arranged such that in operation the tension spring 44 pulls the second end 40 of the beam 36, the beam 36 rotates around the pivot 42 and the first end 38 of the beam 36 moves towards the component 11 such that the isolation element 17 in the recess in the first end 38 of the beam 36 abuts the node line on the component 11. Again the test arrangement 30 allows for axial movement, towards the component 11, and lateral movement of the isolation element 17. Thus the beam 36 forms a housing the for the isolation element 17.

In FIG. 1 the spring 21 is arranged within the housing 18, the isolation element 17 projects from the housing 18 and the isolation element 17 is suspended upon the spring 21. In FIG. 3 the spring 44 is arranged outside the housing or beam 36, the isolation element 17 projects from the housing 36 and the housing 36 and isolation element 17 are suspended upon the spring 44. In both embodiments of the present invention the spring is arranged to bias the isolation element into contact, or abutment, with the component to isolate the vibration modes not of interest.

The fatigue testing and isolation device may be used for testing of any type of aerofoil e.g. fan blades, compressor blades or turbine blades of gas turbine engines.

The component to be tested is held within a fixture, more particularly one end of the component is held in the fixture, and in the case of an aerofoil, e.g. a fan blade, a compressor blade or a turbine blade, the root of the blade is held in the fixture. The component is vibrated using any suitable means of producing vibrations, for example a device to produce high velocity gas, or air, jets which area directed onto the aerofoil or a shaker device such as an electrodynamic, piezoelectric or magnetostrictive actuator. The component is tested by vibration for fatigue testing or high cycle fatigue testing.

The invention claimed is:
1. A fatigue test arrangement comprising:
means to hold a first end of a component while a second end of the component is unrestrained and free to vibrate;
means to vibrate the component;
a vibration isolation device arranged in use to engage the component upon a node line of a mode of vibration to isolate that mode of vibration requiring investigation;
wherein
the isolation device comprises a housing to provide an isolation element;

the isolation element is suspended upon a spring element that is arranged within the housing to allow axial displacement of the isolation element relative to the housing, the spring element being arranged to bias the isolation element into contact with the component;

the isolation element is captured within the housing and projects from an isolation element end of the housing; and the housing about the isolation element is arranged to allow lateral movement of the isolation element relative to the direction of axial displacement.

2. An arrangement as claimed in claim 1 wherein the spring is a mechanical coil spring, a hydraulic spring, a pneumatic spring or a foam element.

3. An arrangement as claimed in claim 1 wherein the isolation element is made from rubber.

4. An arrangement as claimed in claim 1 wherein the isolation element has an edge or has a pointed end.

5. An arrangement as claimed in claim 1 wherein the isolation element end has a gap between the isolation element and an aperture in the isolation element end to allow the lateral movement.

6. An arrangement as claimed in claim 1 wherein the isolation element end is flexible to allow the lateral movement.

7. An arrangement as claimed in claim 1 where the arrangement includes a tensioner mechanism.

8. An arrangement as claimed in claim 7 wherein the tensioner mechanism comprise a loading plate associated with the spring element and a displacement element to vary the load applied to the spring.

9. An arrangement as claimed in claim 8 wherein the displacement element is a screw thread member.

10. An arrangement as claimed in claim 1 wherein the arrangement incorporates a vibration excitation mechanism.

11. An arrangement as claimed in claim 10 wherein the vibration excitation mechanism comprises at least one high velocity gas jet directed towards the component in use.

12. An arrangement as claimed in claim 1 wherein the isolation element abuts the spring element.

13. A fatigue test arrangement comprising:
a holding device arranged in use to hold a first end of a component while a second end of the component is unrestrained and free to vibrate;
a vibration device arranged in use to vibrate the component;
a vibration isolation device arranged in use to engage the component upon a node line of a mode of vibration to isolate that mode of vibration requiring investigation; wherein
the isolation device comprises a housing to provide an isolation element;
the isolation element and the housing are suspended upon a spring element that is arranged outside the housing to allow axial displacement the spring element being arranged to bias the isolation element into contact with the component;
the isolation element projects from an isolation element end of the housing; and
the housing about the isolation element being arranged to allow lateral movement of the isolation element relative to the direction of axial displacement.

14. A fatigue test arrangement comprising:
a holding device arranged in use to hold a first end of a component while a second end of the component is unrestrained and free to vibrate;
a vibration device arranged in use to vibrate the component;
a vibration isolation device arranged in use to engage the component upon a node line of a mode of vibration to isolate that mode of vibration requiring investigation; wherein
the isolation device comprises a housing to provide an isolation element;
the isolation element is suspended upon a spring element that is arranged within the housing to allow axial displacement of the isolation element relative to the housing, the spring element being arranged to bias the isolation element into contact with the component;
the isolation element is captured within the housing and projects from an isolation element end of the housing; and
the housing about the isolation element being arranged to allow lateral movement of the isolation element relative to the direction of axial displacement.

* * * * *